United States Patent [19]  
McAleer et al.

[11] 4,338,335  
[45] Jul. 6, 1982

[54] VACCINE STABILIZER CONTAINING L-GLUTAMIC ACID AND L-ARGININE

[75] Inventors: William J. McAleer, Ambler; Henry Z. Markus, Wyncote, both of Pa.

[73] Assignee: Merck & Co., Inc., Rahway, N.J.

[21] Appl. No.: 173,534

[22] Filed: Jul. 30, 1980

Related U.S. Application Data

[60] Division of Ser. No. 118,703, Feb. 5, 1980, abandoned, which is a continuation-in-part of Ser. No. 89,068, Oct. 29, 1979, abandoned.

[51] Int. Cl.³ .................. A61K 39/12; A61K 39/165; A61K 39/13; A61K 39/245
[52] U.S. Cl. ..................................... 424/361; 424/89; 435/235
[58] Field of Search ................. 424/89, 361; 435/235-239

[56] References Cited

U.S. PATENT DOCUMENTS

| | | | |
|---|---|---|---|
| 2,879,202 | 12/1959 | Aiston | 424/89 |
| 2,946,724 | 12/1960 | Valentine | 424/89 |
| 3,133,861 | 12/1964 | Schwartz | 424/89 |
| 3,143,470 | 12/1964 | Wilner | 424/89 |
| 3,156,620 | 12/1964 | Sharpless | 424/89 |
| 3,214,340 | 12/1965 | Lave | 424/89 |
| 3,322,632 | 12/1967 | Schweinsberg et al. | 424/89 |
| 3,422,188 | 12/1969 | Cabasso | 424/89 |
| 3,629,399 | 12/1971 | Mauler et al. | 424/89 |
| 3,783,098 | 1/1974 | Calnek et al. | 424/89 |
| 3,880,993 | 4/1974 | Gilker | 424/89 |
| 4,147,772 | 4/1979 | McAleer et al. | 424/89 |
| 4,273,762 | 6/1981 | McAleer et al. | 424/89 |

FOREIGN PATENT DOCUMENTS

| | | | |
|---|---|---|---|
| 2405675 | 8/1974 | Fed. Rep. of Germany | 424/89 |
| 2076787 | 10/1971 | France | 424/89 |
| 48-10523 | 4/1973 | Japan | 424/89 |
| 4760867 | 2/1974 | Japan | 424/89 |

OTHER PUBLICATIONS

McAleer at al. Chem. Abstr. 95 #68007Z (1981) of Eur. Pat. Appl. 28,563, May 13, 1981, "Stabilizer For Liquid Vaccines".
Merck and Co., Inc. Chem. Abstr. 92 #135397e (1980) of Neth. Appl. 78 03891, Oct. 16, 1979, "Vaccine Stabilizer".
McAleer et al. Chem. Abstr. 93 #80039c (1980) of S. African 78 02,123, Nov. 28, 1979, "Vaccine Stabilizer".
Chem. Absts. 76:144799j (1972).
Chem. Absts. 67:42097a (1967).
Chem. Absts. 80:41031f (1974).
Contract AID/afr-c-1192, Aug. 28, 1978.

Primary Examiner—Shep K. Rose
Attorney, Agent, or Firm—Donald J. Perrella; Hesna J. Pfeiffer

[57] ABSTRACT

An improved stabilized liquid live viral vaccine contains a live virus, partially hydrolyzed gelatin, a monosaccharide or disaccharide, a cell culture medium, L-glutamic acid, L-arginine and sufficient physiologically acceptable acidic buffer to maintain the pH at from about 6.0 to about 6.5.

4 Claims, No Drawings

VACCINE STABILIZER CONTAINING L-GLUTAMIC ACID AND L-ARGININE

RELATED APPLICATION

The present application is a division of application Ser. No. 118,703 filed Feb. 5, 1980, now abandoned, which application in turn was a continuation-in-part of application Ser. No. 89,068 filed Oct. 29, 1979, now abandoned.

BACKGROUND OF THE INVENTION

The present invention relates to liquid viral vaccines. More particularly it relates to a stabilizer for liquid viral vaccines.

Due to the worldwide distribution of vaccines and the diversity of ambient temperatures, there has been a need to stabilize these preparations for transportation and use. Several stabilization methods have been used in the past.

(a) Low temperatures ($-10°$ C. to $-70°$ C.).

The need for low temperature storage facilities which are not always available limits the practicality of this approach.

(b) Lyophilization

Although lyophilization suffers the disadvantages of being an expensive procedure, lyophilized vaccines are reasonably stable and are stored at $4°-8°$ C. until needed. During this storage period, however, the vaccine slowly deteriorates until after about 12-24 months it does not have sufficient titer to confer immunization. Furthermore, since the lyophilized vaccine must be reconstituted prior to use, the liquid reconstituted preparation loses potency while standing at room temperature. This can result in insufficient titer to confer immunity and results in failure of immunization program.

(c) Stabilizers

These are chemical compounds added to the vaccine and are used in conjunction with either lower temperature storage or lyophilization methods. Chemical stabilizers, e.g., SPGA (a stabilizer described by Bovarnick et al., J. Bact. 59:509-522 (1950), the disclosure of which is incorporated herein by reference) and the like are described in the prior art. As described by Bovarnick et al. a liter of SPGA contains 0.218 M sucrose (74.62 g), 0.00376 M $KH_2PO_4$ (0.52 g), $K_2HPO_4$ 0.0071 M (1.25 g), potassium glutamate 0.0049 M (0.912 g) and 1% serum albumin (10 g). Various modifications of the foregoing amounts of ingredients of SPGA are known to those skilled in the art and sodium glutamate is frequently substituted for potassium glutamate, but the modified compositions are still designated as SPGA. For example, U.S. Pat. No. 3,783,098 refers to an SPGA stabilizer containing monosodium glutamate rather than monopotassium glutamate (col. 6, lines 5-11). U.S. Pat. No. 4,002,256 describes an SPGA stabilizer containing per liter of sterile distilled water, 74.62 g sucrose, 0.45 g $KH_2PO_4$, 1.35 g $K_2HPO_4$, 0.956 g monosodium L-glutamate, and 40 ml of a 25% solution of albuminosol (human albumin). In general an SPGA stabilizer contains from about 2 to about 10% of sugar, e.g. sucrose; from about 0.05 to about 0.3% of a mono- or dibasic alkali metal phosphate salt or mixture thereof, e.g. $KH_2PO_4$, $K_2HPO_4$, $NaH_2PO_4$, or $Na_2HPO_4$, from about 0.05 to about 0.2% of a glutamic acid alkali metal salt, e.g. sodium or potassium glutamate; and from about 0.5% to about 2% serum albumin, e.g. bovine serum albumin or human albumin. Various substitutions of ingredients in the formulation of SPGA stabilizer can be made. For example, a starch hydrolysate, e.g. glucose or dextran may be substituted wholly or partly for sucrose as disclosed in U.S. Pat. No. 3,783,098, (col. 3, lines 59-61) and casein or PVP may be substituted wholly or partly for albumin as described, respectively, in U.S. Pat. No. 3,783,098 (col. 3, line 8) and U.S. Pat. No. 3,915,794. None of the prior art stabilizers, however, imparts the desired enhanced sustained level of stability.

OBJECTS OF THE INVENTION

It is, accordingly, an object of the present invention to provide an improved chemical stabilizer for liquid viral vaccines. Another object is to provide a method for stabilizing liquid viral vaccines. A further object is to provide liquid viral vaccines having prolonged storage stability with diminished reduction in titer. These and other objects of the present invention will be apparent from the following description.

SUMMARY OF THE INVENTION

An improved stabilized liquid live viral vaccine contains a live virus, partially hydrolyzed gelatin, a monosaccharide or disaccharide, a cell culture medium, L-glutamic acid, L-arginine and sufficient physiologically acceptable acidic buffer to maintain the pH at from about 6.0 to about 6.5.

DETAILED DESCRIPTION

The present invention is directed to a stabilized vaccine composition in liquid form containing a live virus, partially hydrolyzed gelatin, a monosaccharide or disaccharide, a cell culture medium, L-glutamic acid, L-arginine and sufficient physiologically acceptable acidic buffer to maintain the pH at from about 6.0 to about 6.5. The liquid vaccine may be obtained by thawing a frozen vaccine or by reconstituting a lyophilized vaccine. Examples of live virus are measles, mumps or rubella, varicella, polio, or hepatitis and the like, or a combination of any two or more of such viruses. Hydrolyzed gelatin is employed to provide a soluble, non-gelling proteinaceous matrix with little or no pyrogenicity or antigenicity.

By partially hydrolyzed gelatin is meant gelatin which has been subjected to partial hydrolysis to yield a partially hydrolyzed gelatin having a molecular weight of about 3,000. This gelatin hydrolysis product has approximately the same amino acid composition as gelatin. Unlike gelatin which forms gels but is insoluble in cold water, hydrolyzed gelatin does not gel but is soluble in cold water, and other common liquids such as milk and orange juice. Aqueous solutions containing up to about 10% hydrolyzed gelatin do not increase appreciably in viscosity. Above about 10% concentration, viscosity increases slowly. At about 50% concentration, solutions are quite viscous. The typical amino-acid composition of hydrolyzed gelatin follows:

| | |
|---|---|
| Alanine | 8.5% |
| Arginine | 7.9% |
| Aspartic Acid | 5.7% |
| Cystine | 0.08% |
| Glutamic Acid | 9.5% |
| Glycine | 22.8% |
| Histidine | 0.77% |
| Hydroxy Proline | 13-14% |
| Isoleucine | 1.3% |

| | |
|---|---|
| Leucine | 2.9% |
| Lysine | 4.2% |
| Methionine | 0.78% |
| Phenyl Alanine | 2.0% |
| Proline | 13.8% |
| Serine | 3.3% |
| Threonine | 1.9% |
| Tyrosine | 0.40% |
| Valine | 2.4% |

Partially hydrolyzed gelatin may be obtained by enzymatic hydrolysis of gelatin by means of a proteolytic enzyme, such as, for example, papain, chymopapain and bromelin, although other known hydrolysis means may be employed, e.g. acid hydrolysis. A suitable hydrolyzed gelatin is obtainable from Wilson and Co., Inc., Calumet City, Illinois under the trade name SOL-U-PRO.

The stabilizer also includes a monosaccharide, e.g., sorbitol, or a disaccharide, e.g., sucrose, lactose, or maltose. Sucrose is preferred.

The L-glutamic acid may be used as such or in the form of its sodium salt, monosodium glutamate.

The L-arginine may be used as such or in the form of its hydrochloride salt.

The acidic buffer may be any physiologically acceptable buffer which will maintain the desired pH of from about 6 to about 6.5, for example, phosphate buffer, acetate buffer or citrate buffer. Phosphate buffer is preferred. The stabilizer is diluted with from about 3 to about 8 times, preferably about 5.5 times, its weight of distilled water before use.

By a cell culture medium is meant a nutrient medium which permits growth of cells in vitro. Some specific nutrient media are, for example, Medium 199, Morgan et al., Proc. Soc. Exp. Biol. & Med., 73:1-8, 1950; Basal Medium Eagle, Eagle, Science, 122, 501-504, 1955; In Vitro, Vol. 6, No. 2, 1970; Dulbecco's Modified Eagle's Medium, Dulbecco et al., Virology, 8, 396, 1959; Smith et al., J. Virol., 12, 185-196, 1960; In Vitro, Vol. 6, No. 2, 1970; Minimum Essential Medium (Eagle), Science, 130, 432 (1959) and RPMI Media, Moore et al., 199, 519-524, 1967; In Vitro, Vol. 6, No. 2, 1970.

The stabilizer of the present invention is applicable to various liquid virus vaccines such as, for example, measles, mumps, rubella, respiratory syncytial, parainfluenza types 1, 2 and 3, and cytomegalovirus.

The stabilizer composition of the present invention contains the following ingredients in about the amounts indicated:

| Ingredient | Parts by weight/50 ml |
|---|---|
| Partially hydrolyzed gelatin | 1.5-2.1 |
| Monosaccharide or disaccharide | 7.0-13.0 |
| Nutrient medium (solids) | 0.4-0.6 |
| L-Glutamic acid | 0.35-0.7 |
| L-Arginine | 0.75-1.3 |
| Physiologically acceptable buffer to adjust pH to 6.0-6.5 | 0.05-0.2 M |

Specific preferred formulations of the liquid viral vaccine stabilizer of the present invention follow:

| | | |
|---|---|---|
| Partially hydrolyzed gelatin | 1.8 | g |
| Sucrose or Sorbitol | 10.0 | g |
| Medium 199 | 0.55 | g |
| Monosodium glutamate | 0.5 | g |
| L-Arginine HCl | 1.0 | g |
| Sodium phosphate buffer, 1M, pH 6.2 | 5 | ml |
| Water, q.s. to | 50.0 | ml |

In addition the stabilizer optionally but preferably contains a small amount of $NaHCO_3$ and of phenol red. In the case of the foregoing formulation the $NaHCO_3$ may be present in an amount of about 1.2 g and the phenol red in an amount of about 0.01 g. While particular formulations have been described above it is to be understood that variations in ratios and concentration of each ingredient are contemplated. One volume of bulk vaccine is usually diluted with from about 2 to about 12 volumes of stabilizer.

The following examples illustrate the present invention without, however, limiting the same thereto.

EXAMPLE 1

40 Ml. of measles viral concentrate which has been stored at $-70°$ C. is thawed in a water bath at 25° C. and then kept at 4°-8° C. The liquid viral concentrate is then split into two aliquots each 16.5 ml.

(A) One 16.5 ml aliquot from this virus fluid is diluted in 50 ml of the following stabilizer which has been sterilized by passing through a 0.2 $\mu$m membrane.

| | |
|---|---|
| 1M Phosphate buffer, pH 6.2 | 5.0 ml |
| Sorbitol, 25% aqueous solution | 7.1 ml |
| Hydrolyzed gelatin, 25% aqueous solution | 7.1 ml |
| Medium 199 | 30.7 ml |

Formulation is carried on under aseptic conditions and laminar flow hood. To prevent microbial growth, Neomycin (0.1 ml, 2500 units) is added to the preparation. The diluted vaccine is dispensed into 2 ml glass ampules (0.7 ml vaccine per ampule) which are immediately flame sealed and stored at 37° C.

(B) The second 16.5 ml aliquot is handled as the first, except that the stabilizer formulation additionally contains 0.5 g monosodium glutamate 1.0 g L-arginine HCl and 10 g sucrose instead of sorbitol.

The storage stability of the vaccines is described in the following table:

| | Titers[1] of Liquid Vaccines Stored at 37° C. | |
|---|---|---|
| Time | Stabilizer of Formulation A | Stabilizer of Formulation B |
| 0 | 3.9 | 3.7 |
| 24 hours | 2.3 | 3.1 |
| 48 hours | 2.0 | 2.7 |
| 72 hours | 1.5 | 2.5 |

[1]Titers are expressed as $TCID_{50}/0.1$ ml.

EXAMPLE 2

25 Ml of measles viral concentrate which has been stored at $-70°$ C. is thawed in a water bath at 25° C. and then kept at 4°-8° C. The liquid viral concentrate is diluted in 75 ml of the B stabilizer formulation (Example 1) and dispensed into 2 ml glass ampules. The ampules are heat sealed and stored at 2°–8° C. The storage stability of the vaccine is described in the following table.

Stability of liquid vaccine stored at 2–8° C.

| Time (months) | Titer (TCID$_{50}$/0.1 ml) |
| --- | --- |
| 0 | 3.7 |
| 1 | 4.1 |
| 2 | 3.1 |
| 4 | 3.5 |
| 6 | 3.3 |

EXAMPLE 3

The following table compares the stability of four lots of liquid measles vaccines prepared at varying times using the stabilizers of formulation A or B as described in Example 1.

| Lot | Stabilizer | Titer (TCID$_{50}$/0.1 ml) after hours indicated at 37° C. | | | |
| --- | --- | --- | --- | --- | --- |
| | | 0 | 24 | 48 | 72 |
| 1 | A | 3.9 | 2.3 | 2.0 | 1.5 |
| 1 | B | 3.7 | 3.1 | 2.7 | 2.5 |
| 2 | A | 4.0 | 3.1 | 2.5 | 1.8 |
| 2 | B | 3.9 | 3.6 | 3.0 | 2.6 |
| 3 | A | 3.9 | — | 2.2 | 2.1 |
| 3 | B | 3.6 | 3.3 | 3.0 | 2.5 |
| 4 | A | 3.5 | 2.1 | 1.6 | 1.5 |
| 4 | B | 3.6 | 3.5 | 3.1 | 2.4 |

What is claimed is:

1. A stabilizer for a liquid vaccine consisting essentially of on a parts by weight basis from about 1.5 to about 2.1 parts partially hydrolyzed gelatin having a molecular weight of about 3,000, from about 7.0 to about 13.0 parts of sorbitol, sucrose, lactose or maltose, from about 0.4 to about 0.6 parts of an in vitro cell culture medium, from about 0.35 to about 0.7 part L-glutamic acid, from about 0.75 to about 1.3 parts L-arginine, and an amount of a physiologically acceptable acidic buffer effective to adjust the pH to from about 6.0 to about 6.5.

2. A stabilizer according to claim 1 wherein the disaccharide is sucrose.

3. A stabilizer according to claim 1 consisting essentially of on a parts by weight basis of about 1.8 parts partially hydrolyzed gelatin having a molecular weight of about 3,000, about 10 parts of a monosaccharide or disaccharide, about 0.5 part of an in vitro cell culture medium, about 0.5 part L-glutamic acid, about 1.0 part L-arginine, and an amount of a physiologically acceptable acidic buffer effective to adjust the pH to from about 6.0 to about 6.5.

4. A stabilizer according to claim 3 wherein the disaccharide is sucrose.

* * * * *